(12) United States Patent
Yang et al.

(10) Patent No.: US 8,394,366 B2
(45) Date of Patent: Mar. 12, 2013

(54) THERMOSENSITIVE POLYMERS FOR THERAPEUTIC USE AND METHODS OF PREPARATION

(75) Inventors: Yi Yan Yang, Singapore (SG); Li Shan Wang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1445 days.

(21) Appl. No.: 10/564,401

(22) PCT Filed: Apr. 15, 2004

(86) PCT No.: PCT/SG2004/000094
§ 371 (c)(1),
(2), (4) Date: Jan. 11, 2006

(87) PCT Pub. No.: WO2005/007717
PCT Pub. Date: Jan. 27, 2005

(65) Prior Publication Data
US 2006/0204555 A1    Sep. 14, 2006

Related U.S. Application Data
(60) Provisional application No. 60/488,093, filed on Jul. 18, 2003.

(51) Int. Cl.
*A61K 31/74* (2006.01)
*A61F 13/00* (2006.01)
(52) U.S. Cl. ...................................... 424/78.27; 424/443
(58) Field of Classification Search ......................... None
See application file for complete search history.

(56) References Cited

U.S. PATENT DOCUMENTS

| | | | |
|---|---|---|---|
| 4,806,609 A | 2/1989 | Tracy et al. | |
| 5,294,692 A | 3/1994 | Barron et al. | |
| 5,296,627 A * | 3/1994 | Tang et al. | 558/34 |
| 5,399,618 A | 3/1995 | Jenkins et al. | |
| 5,410,016 A | 4/1995 | Hubbell et al. | |
| 5,587,143 A | 12/1996 | Wong | |
| 5,721,313 A | 2/1998 | Yeung et al. | |
| 5,874,495 A | 2/1999 | Robinson | |
| 6,107,397 A | 8/2000 | Blankenburg et al. | |
| 2002/0120015 A1 | 8/2002 | Dennis et al. | |
| 2002/0187182 A1 | 12/2002 | Kramer et al. | |

FOREIGN PATENT DOCUMENTS

| | | |
|---|---|---|
| CN | 1206013 A | 1/1999 |
| EP | 217485 | 4/1987 |
| WO | WO 95/24430 | 9/1995 |
| WO | WO 97/05185 | 2/1997 |
| WO | WO 02/96469 A2 | 5/2002 |

OTHER PUBLICATIONS

Vakkalanka et al., Polymer Bulletin, 1996, 36, pp. 221-225.*
Liu et al., Langumuir, 1997, 13, pp. 6421-6426.*
Gan et al., Polymer, 1997, 38(21), pp. 5339-5345.*
Lee et al., J. App. Polymer Sci., 1999, 71, pp. 221-231.*

(Continued)

*Primary Examiner* — Brian Gulledge
(74) *Attorney, Agent, or Firm* — Klarquist Sparkman, LLP

(57) ABSTRACT

A process for preparing a thermosensitive polymer from a microemulsion is provided. The microemulsion comprises a monomer capable of forming a thermosensitive polymer and a polymerizable surfactant. Additional comonomers may be included in the microemulsion to vary the properties of the polymers produced. The resulting thermosensitive polymers may be nanoporous. The polymers according to the invention are suitable for use in medical applications, including use as a wound dressing and for delivery of cells to a graft site.

18 Claims, 7 Drawing Sheets

OTHER PUBLICATIONS

Candau, F. et al., "Polymerization in Nanostructured Media: Applications to the Synthesis of Associative Polymers", Macromolecular Symposia, Mar. 2002, pp. 13-25, vol. 179, Issue 1.

Puig, L.J. et al., "Microstructured Polyacrylamide Hydrogels Prepared Via Inverse Microemulsion Polymerization", Journal of Colloid and Interface Science, Mar. 15, 2001, pp. 278-282, vol. 235, Issue 2.

Munshi, N. et al., "Size Modulation of Polymeric Nanoparticles under Controlled Dynamics of Microemulsion Droplets", Journal of Colloid and Interface Science, Jun. 15, 1997, vol. 190, Issue 2.

Qutubuddin, S. et al., "Novel polymeric composites from microemulsions", Polymer, Oct. 1994, pp. 4606-4610, vol. 35, Issue 21.

Shin, Y. et al., "Hybrid nanogels for sustainable positive thermosensitive drug release", Journal of Controlled Release, May 18, 2001, pp. 1-6, vol. 73, Issue 1.

Nuno-Donlucas, S.M. at al., "Microstructured polyacrylamide hydrogels made with hydrophobic nanoparticles", Journal of Colloid and Interface Science, Feb. 1, 2004, pp. 94-98, vol. 270, Issue 1.

Cochrane, C., et al. Application of an in vitro model to evaluate bioadhesion of fibroblasts and epithelial cells to two different dressings. Biomaterials. (1999). pp. 1237-1244. vol. 20, Issue 13.

Rothe, M. and Falanga, V. Growth Factors. Their biology and promise in dermatologic diseases and tissue repair. Arch Dermatol. (1989). pp. 1390-1398. vol. 125, Issue 10.

Purna, S.K. and Babu, M. Collagen based dressings—a review. Burns. Feb. 2000. pp. 54-62. vol. 26, Issue 1.

Pruitt, B.A. and Levine, N.S. Characteristics and uses of biologic dressings and skin substitutes. Arch Surg. (1984). pp. 312-322. vol. 119, Issue 3.

Takezawa, T., et al. Cell culture on a thermo-responsive polymer surface. Biotechnology (NY). Sep. 1990. pp. 854-856. vol. 8, Issue 9.

Lin, Shan-Yang, et al. Design and evaluation of drug-loaded wound dressing having thermoresponsive, adhesive, absorptive and easy peeling properties. Biomaterials. Nov. 15, 2001. pp. 2999-3004. vol. 22, Issue 22.

Ruiz-Cardona, L., et al. Application of benzyl hyaluronate membranes as potential wound dressings: evaluation of water vapour and gas permeabilities. Biomaterials. 1996. pp. 1639-1643. vol. 17, Issue 16.

Queen, D., et al. The preclinical evaluation of the water vapour transmission rate through burn wound dressings. Biomaterials. Sep. 1987. pp. 367-371. vol. 8, Issue 5.

Liu, J., et al. J. Macromol. Sci, Pure Appl. Chem. (1996) A33, 3: 337.

Ichikawa, H., et al. Coating performance of aqueous composite latices with N-isopropylacrylamide shell and thermosensitive permeation properties of their microcapsule membranes. Chemical and Pharmaceutical Bulletin. 1996. pp. 383-391. vol. 44, Issue 2.

Sun, YM, et al. Temperature-sensitive latex particles for immobilization of a-mylase. Journal of Dispersion Science and Technology. 1999. pp. 907-920. vol. 20, Issue 3.

Chen-Jyh-Ping, and Su, Da-Rong. Latex Particles with Thermo-Flocculation and Magnetic Properties for Immobilization of a-Chymotrypsin. Biotechnology Progress. (2001) pp. 369-375. vol. 17, Issue 2.

Vakkalanka, SK and Peppas, NA. Swelling behavior of temperature- and pH-sensitive block terpolymers for drug delivery. Polymer Bulletin. (1996) pp. 221-225. vol. 36, Issue 2.

Vakkalanka, Sk, et al. Temperature- and pH-sensitive terpolymers for modulated delivery of streptokinase. Journal of Biomaterials Science-Polymer Edition. (1996) pp. 119-129. vol. 8, Issue 2.

Lee, Wen-Fu and Shieh, Chih-Hsuan. pH-thermoreversible hydrogels. I. Synthesis and swelling behaviors of the (N-isopropylacrylamide-co-acrylamide-co-2-hydroxyethyl methacrylate) copolymeric hydrogels. Journal of Applied Polymer Science. (1999) pp. 221-231. vol. 71, Issue 2.

Lee, Wen-Fu and Huang, Yu-Lin. Thermoreversible hydrogels XIV. Synthesis and swelling behavior of the (n-isopropylacrylamide-co-2-hydroxyethyl methacrylate) copolymeric hydrogels. Journal of Applied Polymer Science. (2000) pp. 1769-1781. vol. 77, Issue 8.

Sun, Yi-Ming, et al. Preparation and characterization of a-amylase-immobilized thermal-responsive composite hydrogel membranes. Journal of Biomedical Materials Research, (1999) pp. 125-132. vol. 45, Issue 2.

Burke, JF. Observations on the development and clinical use of artificial skin—an attempt to employ regeneration rather than scar formation in wound healing. Jpn. J. Surg. Nov. 1987. pp. 431-438. vol. 17, Issue 6.

Biasia, J., et al. Microemulsions: structure and Dynamics (Eds: Friberg SE, Bothorel P) CRC Press, 1997, Ch. 1.

Chow, P.Y. and Gan, L.M. Microemulsion processing of silica-polymer nanocomposites. J Nanosci Nanotechnol. Jan.-Feb. 2004. pp. 197-202. vol. 4, Issues 1-2.

James, J.H. and Watson, A.C. The use of Opsite, a vapour permeable dressing, on skin graft donor sites. Br. J. Plast. Surg. Apr. 1975. pp. 107-110. vol. 28, Issue 2.

Lee, Bae Hoon, et al. Synthesis and Characterization of Thermosensitive Poly(organophosphazenes) with Methoxy-Poly-(ethylene glycol) and Alkylamines as Side Groups. Bull. Korean Chem. Soc. 2002. vol. 23, No. 4. pp. 549-554.

Sarkis, C., et al. Efficient transduction of neural cells in vitro and in vivo by a baculovirus-derived vector. PNAS. Dec. 2000. vol. 97, No. 26. pp. 14638-14643.

Jean, B., et al. Interaction of a thermosensitive polymer with surfactant at the air-water interface. http://www-llb.cea.fr/activ9798/chem-phys-bio/polymer_at_the_air-water_interface.pdf. As of Apr. 15, 2004. pp. 86-89.

Tichagwa, L., et al. Selected acrylate and acrylamide-based surfmers and polysoaps and their use in emulsion polymerisation. http://academic.sun.ac.za/unesco/Conferences/Conference2002/Tichagwa%20(8).pdf. As of Apr. 15, 2004. p. 1 (abstract).

Nippon Kagaku Kaishi, 11 (1995) 909-915.

Communication Pursuant to Article 94(3) EPC, dated May 26, 2009, European Patent Application No. 04 727 779.3.

Office Action, dated Aug. 7, 2009, issued in CN Application No. 200480020822.0.

Antonietti, M. et al., "Morphology Variation of Porous Polymer Gels by Polymerization in Lyotropic Surfactant Phases", Macromolecules, 1999, pp. 1383-1389, vol. 32.

EP Office Action dated Jan. 4, 2010 issued in corresponding European Patent Application No. 04727779.3.

JP Office Action dated Oct. 27, 2009 issued in corresponding Japanese Patent Application No. 2006-520144 (with English translation).

EP Office Action dated Aug. 30, 2010 issued in corresponding European Patent Application No. 04727779.3.

Laukkanen, A. et al., "Poly(N-vinylcaprolactam) Microgel Particles Grafted with Amphiphilic Chains", Macromolecules, 2000, pp. 8703-8708, vol. 33.

Serizawa, T. et al., "Rapid and Controlled Deswelling of Porous Poly(N-isopropylacrylamide) Hydrogels Prepared by the Templating of Interpenetrated Nanoporous Silica Particles", Journal of Polymer Science: Part A: Polymer Chemistry, 2002, pp. 6542-3547, vol. 40.

Office Action (4th), dated Oct. 27, 2009, issued in corresponding People's Republic of China Patent Application No. 200480020822 and English-language text translation.

Allen et al., "Interaction of soft condensed materials with living cells: Phenotype/transcriptome correlations for the hydrophobic effect," Proceedings of the National Academy of Sciences of the United States of America, 100(11):6331-6336, 2003.

* cited by examiner

THERMOSENSITIVE POLYMERS FOR THERAPEUTIC USE AND METHODS OF PREPARATION

CROSS REFERENCE TO RELATED APPLICATION

This claims the benefit of U.S. Provisional Application No. 60/488,093, filed Jul. 18, 2003.

FIELD OF THE INVENTION

The present invention relates generally to polymeric materials and methods of their preparation, including nanoporous polymers suitable for use in medical applications such as wound dressing and cell grafting.

BACKGROUND OF THE INVENTION

Wound healing is an active area of interest for many researchers given its importance in the treatment of burns, the prevention of post surgical adhesions and in cosmetic surgery. The objective of using a wound dressing is to accelerate wound healing by preventing excessive fluid loss and bacterial infection, and by promoting the acceleration of tissue regeneration (T. Stephen, in *Wound management and dressings*, The Pharmaceutical Press, London, (1990), 1.).

Currently, available dressing materials tend to be composed of gauze, which frays easily. The fibers of the gauze tend to become trapped in the nascent tissue of healing wounds, making the eventual removal of the dressing extremely difficult and painful. This would also likely tear off fibroblasts or epithelial cells that might have proliferated and migrated onto the dressing material, thereby compromising the normal healing process by inflicting secondary damage to the wound (Cochrane et al. *Biomaterials* (1999) 20: 1237.). This is often the case when a dressing has to be changed routinely.

SUMMARY OF THE INVENTION

In one aspect, the present invention provides a process for preparing a thermosensitive polymer comprising polymerizing a microemulsion comprising a first monomer that is capable of forming a thermosensitive polymer and a polymerizable surfactant.

In another aspect, the present invention provides a method of dressing and undressing a wound comprising applying a thermosensitive polymer to a wound; immediately prior to removing the polymer from the wound, reducing the temperature of thermosensitive polymer to facilitate removal of the polymer, and removing the polymer from the wound.

In yet another aspect, the present invention provides a method of delivering a therapeutic agent to a wound comprising incorporating a therapeutic agent into a thermosensitive nanoporous polymer; and applying the thermosensitive nanoporous polymer to the wound.

In a further aspect, the present invention provides a method of delivering a cell to a graft site comprising culturing the cell on a thermosensitive nanoporous polymer, and placing the polymer comprising the cell onto the graft site.

In yet a further aspect, the present invention provides a thermosensitive polymer which is nanoporous. The invention also provides a thermosensitive nanoporous polymer prepared according to the various embodiments of the process of the present invention. The invention further provides a thermosensitive nanoporous polymer formed from a microemulsion comprising a first monomer capable of forming a thermosensitive polymer and a polymerizable surfactant.

The present invention provides a process for preparing a thermosensitive polymer from a microemulsion. The polymer is useful in medical applications such as wound dressing and for delivery of cells to a graft site.

The invention therefore also relates to use of a thermosensitive polymer according to various embodiments of the invention as a wound dressing and, to deliver a therapeutic agent to a wound and to deliver a cell to a graft site.

The polymer is formed by polymerizing a microemulsion that comprises a monomer capable of forming a thermosensitive polymer and a polymerizable surfactant.

By forming the polymer from a microemulsion incorporating such a monomer, the polymer has thermosensitive swellability characteristics that provide advantages when the polymer is used in the context of a medical application. For example, the polymer may be applied to a wound as a dressing to minimize the risk of bacterial infection. Manipulation of the ambient temperature results in the change of hydrophilicity of the polymer, facilitating removal of the polymer from a wound, and thereby reducing disruption of the healing process at the wound site.

The polymer can be made to be nanoporous, allowing for gaseous exchange and provides thermal insulation. The polymer can also be made to be transparent, as would be known to a skilled person, permitting observation of the wound without the need to remove the dressing prematurely. Furthermore, the polymer of the invention provides a protective barrier that is generally impermeable to microorganisms, thereby helping to minimize risk of infection of the wound.

The porosity of the polymer makes it suitable for delivering therapeutic agents, such as drugs, antibiotics, cellular factors, nucleic acids or peptides to a wound. Incorporating the polymer with a therapeutic agent allows for a sustained release of the therapeutic agent once the polymer is applied to the wound.

The polymer may also be used as a vehicle for the delivery of cultured cells or tissue to a wound or graft site.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which ill embodiments of the present invention by way of example only.

DETAILED DESCRIPTION

Figure 1:
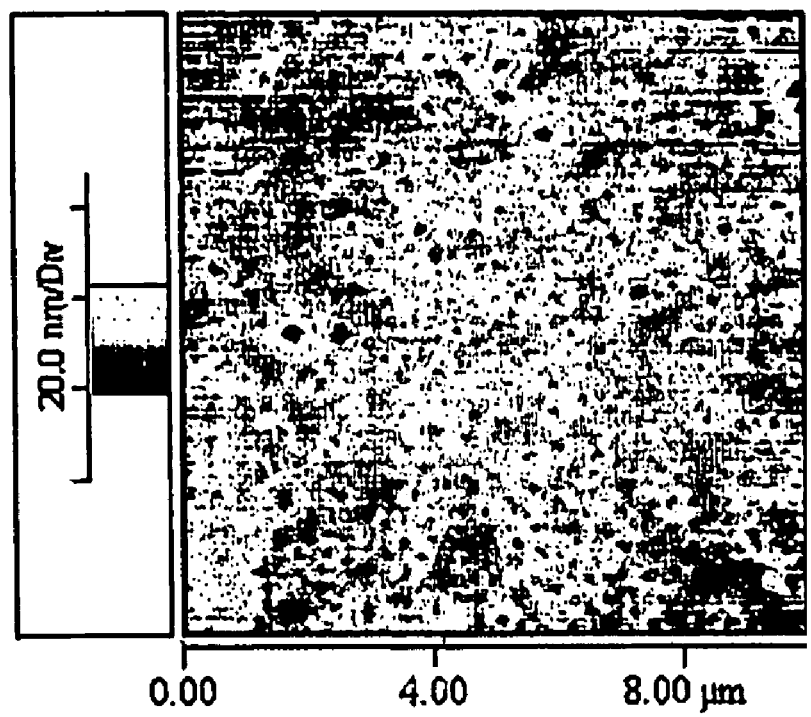
FIG. 1 is an atomic force microscopy image depicting the surface topography of a thermosensitive porous membrane.

Ideally, a wound dressing should be flexible, gas permeable, durable and have the ability to control water loss. It should effect rapid wound closure to prevent sepsis and excessive fluid loss through the open wound. It should adhere well to the wound and be easy to apply and remove without causing damage to the granulation tissue or new epithelium. Preferably, it should be transparent to allow observation of the wound without requiring premature removal of the dressing, which results in interruption of the wound healing process. It should maintain its shape during application to the wound and also be comfortable when in place. In addition, it should not exhibit antigenicity, or local and systemic toxicity. Finally, it should be cost-effective. Despite extensive studies, such material is currently not available (Wiseman et al., in *Wound dressings: Design and use* (Eds: Cohen, Diegelmann and Linndblad) Philadelphia: WB Saunders Co. 1992, 562; Dale, *Prof Nurse* 12 *Suppl,* 1997, 12; Rothe and Falanga, *Arch Dermatol* 1989, 125: 1390; Purna and Babu, *Burns,* 2000, 26: 56; Pruitt and Levine, *Arch Surg* 1984 19: 312).

A thermosensitive polymer such as poly(N-isopropylacrylamide) ("PNIPAAm") exhibits a lower critical solution temperature ("LCST"). PNIPAAm is a well-known thermosensitive polymer that exhibits a well-defined LCST of about 32° C. in water. PNIPAAm is fully hydrated, with an extended chain conformation, in aqueous solutions below 32° C. and is extensively dehydrated and compact above this temperature.

Thermosensitive polymers are polymers that undergo a phase shift when their temperature passes through a lower critical solution temperature ("LCST"). Above the LCST, the polymer tends to become dehydrated, making it less soluble in water. Below the LCST, the polymer becomes extensively hydrated, and is thereby more water-soluble. A number of poly(acrylamide) derivatives, for example, poly(alkylated acrylamides) are thermosensitive, which include, but are not limited to, poly(N-isopropylacrylamide) ("PNIPAAm") or poly(N,N-diethylacrylamide) ("PDEAAm").

In the present context, the term "thermosensitive polymer" refers to a polymer that has an increased affinity for water, and therefore can swell below a given temperature herein referred to as LCST.

A monomer capable of forming a thermosensitive polymer is a monomeric compound that is capable of polymerizing with itself or with other monomeric compounds to form a polymer that is thermosensitive. For example, the monomer may self-polymerize to form a thermosensitive homopolymer, or it may polymerize with another monomeric compound to form a random copolymer or a block copolymer, each of which will exhibit thermosensitive properties.

The inventors have discovered that polymerization of a microemulsion that includes a monomer capable of forming a thermosensitive polymer and a polymerizable surfactant results in a thermosensitive polymer. The polymer therefore has thermosensitive swellability charateristics that provide advantages when the material is used in the context of a medical application. For example, a thermosensitive polymer membrane which is nanoporous may be applied to a wound as a dressing. When the dressing needs to be removed, the membrane may be swollen by reducing the temperature of the wound below the LCST of the polymer, thereby facilitating its removal from the wound site.

Thus, the present invention provides a process for preparing a thermosensitive polymer comprising polymerizing a microemulsion comprising a first monomer capable of forming a thermosensitive polymer and a polymerizable surfactant.

As is understood in the art, "microemulsion" refers to transparent dispersed liquid systems consisting of a hydrophilic solution phase, a hydrophobic solution phase and a surfactant, which is continuous or bi-continuous, the microemulsion having equilibrium domain sizes typically on the order of 1 to 100 nm. The preparation of microemulsions is known in the art and microemulsions including polymerizable surfactants have been used to prepare transparent solid polymers having various nanostructures. A polymerizable surfactant is capable of polymerizing with itself or with other monomeric compounds to form a polymer. Due to the incorporation of the surfactant into the polymer, the need for separation of the surfactant from the polymer after polymerisation can be avoided.

The first monomer and the polymerizable surfactant may be combined with water to form a mixture, which is then dispersed. The mixture may be dispersed to form a microemulsion by standard techniques known to a skilled person to create the microemulsion. For example, the mixture may be sonicated, vortexed, or otherwise agitated to create microdroplets of the different phases within the mixture, the microdroplets being about 1 to about 100 nm in diameter. Or, for example, the mixture can be passed through a filter having pores on the nanometer scale so as to create fine droplets.

The first monomer used in the microemulsion may be any monomer that forms a thermosensitive polymer upon polymerization. Generally, such monomers must be safe for use in the subject and are preferably capable of polymerizing with other monomers, which include, but are not limited to, acrylamide derivatives such as N-isopropylacrylamide and N,N-diethylacrylamide. Additionally, it is highly desirable that the monomer polymerizes to form a nanoporous matrix to enable good gas permeation and sustained release of bioactive agents that may be incorporated in the polymer. A nanoporous matrix can be attained when the components of the microemulsion are in the appropriate ratios so as to form a bi-continuous phase as would be understood by a skilled person. It is further desirable that the monomer be capable of polymerizing in the presence of ultraviolet radiation and a photoinitiator, or of polymerizing in the presence of a redox pair such as ammonium persulfate (APS) and N,N,N',N'-tetramethylethylenediamine (TMEDA), or polymerizing in the presence of heat, for example by thermal polymerization through use of azobisisobutyronitrile (AIBN).

In one embodiment, the first monomer is an acrylamide derivative such as an alkylated acrylamide, for example N-isopropylacrylamide ("NIPAAm") or N,N-diethylacrylamide ("DEAAm"), which polymerize to form poly(N-isopropylacrylamide) ("PNIPAAm") or poly(N,N-diethylacrylamide) ("PDEAAm"), respectively. PNIPAAm is a well-known thermosensitive polymer that exhibits a well-defined LCST of about 32° C. in water. PNIPAAm is fully hydrated, with an extended chain conformation in water below 32° C. and is extensively dehydrated and compact above this temperature. PNIPAAm has been successfully used in cell culture, where its thermo-responsive nature allowed the detachment of cultured cells without the need for enzymatic treatment (Takezawa et al. *Bioetechnol.* (1990) 8: 854.). Once coated with PNIPAAm, the treated culture surface remains hydrophobic until the culture temperature is lowered past the LCST of the PNIPAAm. Moreover, Lin et al. reported that Eudragit E films loaded with PNIPAAm microgel beads showed significantly reduced peel strength between 25° C. and 37° C. This might be attributed to the fact that at 25° C., below the LCST of PNIPAAm, the absorption of fluid by the relatively hydrophilic PNIPAAm microgel beads would have decreased the adhesive property of the films, resulting in the lower peel strength (Lin et al. *Biomaterials* (2001) 22: 2999.). Other exemplary monomers include N-alkylacrylamide, N-alkylmethacrylamide, N-ethylacrylamide, N,N-diethylacrylamide, N-propylacrylamide, N-n-propylmethylacrylamide, N-isopropylacrylamide, N,N-isopropylmethylacrylamide, N-cyclopropylacrylamide, or the anaologous acrylate or methacrylate, hydroxypropyl acrylate-co-acrylamide, diacetone acrylamide-co-hydroxyethyl acrylate, hydroxypropyl acrylate-co-hydroxyethyl acrylate, ethylacrylamide, cyclopropylacrylamide, n-propylacrylamide, or isopropylacrylamide.

The surfactant used in the microemulsion may be any polymerzable surfactant and therefore can copolymerize with the monomer. In different embodiments, the surfactant may be ω-methoxy poly(ethylene oxide)$_{40}$ undecyl α-methacrylate ("$C_1$-PEO-$C_{11}$-MA-40"), or it may be fluronic68-diacrylate.

The microemulsion may further comprise one or more monomers that may or may not form a thermosensitive polymer and which may copolymerize with the first monomer capable of forming a thermosensitive polymer and polymerizable surfactant to form the polymer. A monomer that is included in the microemulsion in addition to the fist monomer capable of forming a thermosensitive polymer is referred to herein as a "comonomer".

The comonomers may include any monomer that will polymerize to form a material suitable for use in medical applications and that can copolymerize with the monomer capable of forming a thermosensitive polymer. In various embodiments, the comonomer comprises methyl methacrylate ("MMA") and/or 2-hydroxyethyl methacrylate ("HEMA"). These comonomers are used to improve or adjust the mechanical strength and hydrophilicity of the resulting polymer, respectively.

As will be appreciated by a skilled person, the precise amount of each of the above ingredients in the microemulsion is not critical, but depends on a number of factors, and may be varied for each ingredient depending on the proportion of the remaining ingredients. For example, a sufficient amount of monomer capable of forming a thermosensitive polymer should be included such that the resulting polymer has the desired thermosensitive properties. Moreover, the LCST for any given polymer may be adjusted by using appropriate comonomers, and by varying the ratio of the comonomer to the first monomer. This means that the discontinuous change in swelling can take place in a different temperature range, as may be desired for a particular application. As well, there should not be too much total monomer content such that the resulting polymer becomes too rigid or inflexible.

The type and ratio of different types of monomers that may be included can be varied so as to influence the properties of the resulting polymer. For example, the hydrophobicity of the polymer can be increased by including increasing amounts of a comonomer or comonomers that are more hydrophobic than the first monomer capable of forming a thermosensitive polymer. A skilled person will understand how to combine different monomers and vary the ratios to determine the effect on the various properties of the resulting membrane, such as the LCST, hydrophobicity and tensile strength.

The ratio of the first monomer to the comonomers in the mixture used to form the microemulsion may vary depending on the desired properties of the resulting polymer. In various embodiments, the ratio is 1:0, 5:3, 3:1, 1:1, or 1:3. By varying the ratio, the thermosensitivity of the resulting membrane, and thus its swelling properties, can be modified as desired.

In one embodiment, the concentrations of the water, polymerizable surfactant and total monomer content in the mixture are between about 15% and about 50%, between about 20% and about 45%, and between about 25% and about 50% (w/w), respectively.

In other embodiments, the process optionally may further comprise a step of cross-linking using a cross-linker. For example, cross-linking may be achieved by chemical cross-linking, photochemical cross-linking, electron beam cross-linking, ultraviolet cross-linking or other methods that would be apparent to a skilled person. The method of cross-linking will depend on the nature of the components of the microemulsion that are to be cross-linked.

For example, when certain surfactants such as $C_1$-PEO-$C_{11}$-MA-40 are used as the polymerizable surfactant, the microemulsion may comprise a chemical cross-linker, such as, for example, ethylene glycol dimethacrylate ("EGDMA"). The chemical cross-linker may be any chemical cross-linker that will cross-link the various components of the microemulsion, for example, any cross-linker that is capable of cross-linking monomers having vinylic or acrylic double bonds. Therefore, the particular cross-linker chosen will depend on the nature of the monomers and polymerizable surfactant in the microemulsion.

In one embodiment, the concentration of the cross-linker is about 5% as a percentage of the weight of the total monomers.

The microemulsion may be polymerized by standard techniques that would be apparent to a skilled person. For example, the microemulsion may be polymerized by heat, the addition of a catalyst, by irradiation of the microemulsion or by introduction of free radicals into the microemulsion. The method of polymerization chosen will be dependent on the nature of the components of the microemulsion.

Polymerization of the microemulsion may involve the use of a catalyst. The catalyst may be any catalyst or polymerization initiator that promotes polymerization between the different types of monomers and the surfactant. The specific catalyst chosen may depend on the particular monomers (the first monomer and any comonomer), and polymerizable surfactant used or the method of polymerization. For example, polymerization can be achieved by subjecting the microemulsion to ultraviolet radiation if a photoinitiator is used as a catalyst. For example, the photo-initiator 2,2-dimethoxy-2-phenylacetophenone may be used, or an alkylaryl ketone may be used.

In one embodiment, the concentration of photoinitiator is between about 0.1% to about 0.3%, as a percentage of the combined weight of total monomers and surfactant.

The microemulsion may be formed into the desired end shape prior to polymerization. For example, a membrane may be formed by pouring or spreading the microemulsion into a thin layer of a desired thickness prior to polymerization of the microemulsion to form the polymer membrane. The microemulsion may also be formed into fibers or tubes, if desired, for example, by pouring the microemulsion into a cast prior to polymerizing. After polymerization, the membrane formed from the polymer may be rinsed and equilibrated with water, and optionally dried and may be sterilized in preparation for use in a medical or clinical application.

The polymer, and resulting membrane, may be nanostructured, meaning that the material possesses regions of ordered structure, these ordered regions being on the nanometer scale, typically between a range of about 1 to about 100 nm. The pores are formed from the volume occupied by water in the microemulsion. Thus, in different embodiments the pores in the material and the resulting membrane have the dimensions of the hydrophilic phase in the microemulsion, about 1 to about 100 nm, about 10 to about 100 nm, about 50 to about 100 nm, or about 50 nm.

When the polymer is formed according to the methods of the invention, the polymer is preferably transparent, such that in use as a wound dressing it allows for visualization of the underlying wound and monitoring of the healing process.

The thermosensitive polymer prepared by the above process is preferably strong, flexible and stretchable. These properties are influenced by the type and amount of monomer used to form the microemulsion. For example, in certain embodiments, inclusion of comonomer HEMA may improve the flexibility of the polymer due to its hydrophilic properties.

In particular embodiments, the tensile strength of the polymer may range from about 4 to about 20 MPa Inclusion of comonomer methyl methacrylate in certain embodiments may reduce the tensile strength of the polymer, but increase elasticity, possibly due to the introduction of a hydrophobic comonomer that allows for hydrophobic interactions between polymer chains. A skilled person can readily vary the different monomer components to achieve the various desired mechanical properties of the polymer.

Fluid retention beneath a wound dressing, caused by poor water vapor permeation, or the dehydration of a granulating wound bed, caused by rapid water loss, can pose serious problems to the healing of wounds. An ideal wound dressing maintains the evaporative water loss from a wound at an optimal rate to prevent both excessive dehydration as well as the accumulation of exudates. A granulating wound experiences an evaporative water loss of about 5138 $g/m^2/day$, as much as 20 times that of skin with a first degree burn.

Wound dressings with very low water vapour transmission rate (WVTR) include, Vigilon®, Vigilon cover film and Stretch 'n' Seals dressings, which have WVTRs of 168±32, 139±23 and 326±44 $g/m^2/day$, respectively (Ruiz-Cardona et al. *Biomaterials* (1996) 17:1639.). Tegaderm® and Bioclusive®, as well as many adhesive film dressings, also have low water vapour transmission rates, with respective WVTRs of 491±44 and 382±26 $g/m^2/day$[15]. OpSite® (WVTR of 426 $g/m^2/day$) is approximately 28 μm thick and has been used as a skin graft donor site dressing with some success, although fluid collections must be removed frequently by puncturing the material and aspirating the fluid.

In contrast, hydrophilic materials such as Geliperm® have high WVTR. Geliperm® has a WVTR of 10972±995 $g/m^2/day$. However, using wound dressings with such a high WVTR could lead to the total dehydration of the wound surface (Queen et al. *Biomaterials* (1987) 8: 367.).

In certain embodiments, the thermosensitive nanoporous membranes described herein may exhibit WVTR values ranging from about 500 to about 2000 $g/m^2/day$. In certain embodiments, the WVTR ranges from about 500 to about 900 $g/m^2/day$. Thus, the polymer may be particularly well suited for use with wounds that incur light evaporative water loss. The WVTR may be affected by the pore size and monomer composition used to prepare the membrane. Thus, by selecting different surfactants or by adjusting the monomer content or water content of the microemulsion, it is possible to adjust the WVTR of a particular nanoporous membrane.

Preferably, the thermosensitive polymer formed by the above process has an LCST that is biologically relevant. That is, the LCST should be in a temperature range such that the temperature of the polymer will be above the LCST when in place, and can be readily lowered below the LCST when the polymer needs to be swelled, without causing harm to the patient The LCST of the membrane is preferably at least slightly below the body temperature of the patient having the wound. In one embodiment, the polymer has an LCST that is below the temperature of the wound site. In one embodiment, the patient having the wound is a human, and the LCST of the membrane is between about 32° C. and 37° C. The LCST of a given polymer can be adjusted by varying the conditions under which the membrane is transitioned below its LCST, for example, by including various salts in the solution applied to membrane during cooling. Typically, the LCST is lower in a solution containing salts.

The swelling property of the polymer and the resulting membrane is temperature dependent in that the polymer swells to a greater extent the further the temperature is below the LCST. The temperature dependency is not necessarily linear, and the polymer may exhibit a discontinuous swelling ratio around the LCST.

The swelling property of the polymer is also dependent on the concentration of first monomer that is used to form the material. Greater concentrations of such a monomer increase the swellability of the material in response to a temperature decrease.

Preferably, the polymer and the resulting membrane are thermostable to allow for sterilization of the membranes prior to use in a medical application. In different embodiments, the polymer has a decomposition temperature, of at least about 300° C. The thermal stability does not appear to be affected by different microemulsion compositions and provides a significant advantage as the membranes can be sterilized, for example by autoclaving, prior to clinical application.

In different embodiments, the resulting polymer is biocompatible, non-cytotoxic and non-allergenic and causes minimal irritation to the tissue at the wound site.

The thermosensitive polymer prepared by different embodiments of the process of the present invention is useful as a wound dressing for closing open wounds that need healing. The wound may be on any animal, for example, without limitation, a mammal, for example, a human. The swelling properties of the membrane make it particularly useful as a wound dressing, as swelling of the membrane prior to removal from the wound when the dressing needs to be changed facilitates removal and minimizes disruption of the healing process.

Thus, there is provided a method of dressing and undressing a wound comprising applying a thermosensitive polymer to a wound; immediately prior to removing the polymer from the wound, reducing the temperature of thermosensitive polymer to facilitate removal of the polymer, and removing the polymer from the wound.

The polymer may be nanoporous and may be applied to the wound in a swelled or unswelled state. If the polymer is to be applied in a swelled state, it is immersed in water prior to application at a temperature below the LCST. Due to the temperature-dependent swelling properties of the polymer, the dressing will contract upon warming.

However, if the polymer is applied in a dry state, for example, when excessive exudates exist in the wound, it is dried prior to application.

In order to remove the dressing with minimal disruption to the healing wound, the temperature of the polymer is lowered, in the presence of water, prior to removal. The lower the temperature to which the polymer is cooled, the greater the swelling of the polymer. The temperature should be a temperature that is sufficient to facilitate removal and which minimizes discomfort to the patient or damage to the tissue at the wound site.

The thermosensitive nanoporous polymer as prepared by different embodiments of the process of the invention may be used to deliver various therapeutic agents to the wound site to promote healing of the wound. For example, it may be desirable to deliver antibiotics, drugs such as anti-inflammatories or clotting agents, hormones involved in wound repair or other biomolecules such as nucleic acids or polypeptides, to the wound site.

Generally, the therapeutic agent may be incorporated within the polymer matrix, which allows for controlled release of the therapeutic agent once the polymer is in place on the wound.

Thus, there is provided a method of delivering a therapeutic agent to a wound comprising incorporating a therapeutic agent into a thermosensitive nanoporous polymer and applying the thermosensitive nanoporous polymer to the wound.

The therapeutic agent may be any agent having a therapeutic or preventative effect on the wound with respect to healing or prevention of infection. For example, without limitation, the therapeutic agent may be a drug, an antibiotic, an anti-inflammatory agent, a clotting factor, a hormone, a nucleic acid, a peptide, a cellular actor, or a ligand for a cell surface receptor.

Preferably the agent will cause minimal irritation to the wound site, and cause minimal interference with the healing process. As well, it is preferred that the therapeutic agent is one that does not interfere with the physical or chemical properties of the thermosensitive nanoporous polymer.

The therapeutic agent may be incorporated into the polymer, for example, by soaking the polymer membrane in a solution containing the agent. Alternatively, if the agent is stable under the particular polymerization conditions that are to be used, it may be incorporated into the nanoporous membrane during the polymerization process.

Varying the composition of the membrane varies the profile of release of the therapeutic agent and the extent of the initial burst release of the therapeutic agent can be altered. Typically, the therapeutic agent is released from the membrane in a sustained release manner.

As well, it is desirable to deliver graft cells or tissue to a wound or other graft site so as to seed the site with healthy growing cells or tissue. The porous nature of the polymer according to different embodiments of the present invention, in combination with its thermosensitive swelling characteristics, contributes to the usefulness of the polymer as a vehicle for delivering cells or tissue to a graft site.

In one aspect, there is provided a method of delivering a cell to a graft site comprising culturing the cell on a thermosensitive nanoporous polymer, and placing the polymer comprising the cell onto the graft site. In various embodiments, the polymer may be coated with hyaluronic acid, collagen or any other biocompatible matrix prior to culturing the cell thereon.

The polymer may be used to deliver a cell, a number of cells, or tissue to the graft site. Thus, "a cell" includes a single cell and a plurality of cells, including a tissue. The cells or tissue may be derived from the patient to whom the graft is being applied, or they may derive from another source. The cells or tissue may be transgenic cells or tissue, where the transgene makes the cells or tissue suitable for gene therapy.

By reducing the temperature of the polymer, the polymer expands and the cells are more readily released from the polymer to the graft site. The polymer may be removed from the graft site after new tissue has formed. Alternatively, the polymer may be removed after an incubation period following transplantation of the cells and polymer, but before new tissue has formed. In one embodiment, the polymer can be swelled prior to application on the graft site.

Various cell types may detach from the polymer at different optimal temperatures. The temperature at which a particular cell type will detach from the polymer may be varied by adjusting the particular monomer types and ratios used to form the polymer.

The graft site may be any graft site, including a wound site, as well as any other accessible site to which it is desired to deliver cells, including the ear and cornea. For example, the polymer may be used to deliver cells to repair the Round Window Membrane in the ear of a subject or to deliver cells for artifical corneal implant.

The polymer of the invention may be advantageously used in other applications where having a material with temperature-dependent swellability characteristics is desirable. For example, the nanoporous polymer may be used as scaffolding for cell or tissue culture, including stem cell culture. Using a thermosensitive nanoporous membrane or fiber as a support for cultured cell growth permits the transfer of the cultured cells without the use of harsh enzymatic or physical disruption to dislodge the cells from the culture vessel. Furthermore, due to the nanoporosity of the polymer, the thermosensitive nanoporous polymer of the invention may be used in separation techniques to filter or separate particles having nanometer dimensions. As well, the polymer may be used to separate cells, by conjugating to the membrane a ligand that can bind the specific type of cell that is to be separated.

The following experiments are illustrative of the process of preparing the thermosensitive polymers and the resulting polymers and the methods of their use and do not limit the broad aspects of the processes, polymers or methods of use as disclosed herein.

EXAMPLES

1. Materials Used

Methyl methacrylate (MMA) and 2-hydroxyethyl methacrylate (HEMA) from Sigma were distilled at reduced pressure. N-Isopropylacrylamide (NIPAAm) was purified by crystallization (n-hexane). Ethylene glycol dimethacrylate (EGDMA), and 2,2-dimethoxy-2-phenylacetophenone (DMPA) from Aldrich were used without further purification. ω-methoxy poly(ethylene oxide)$_{40}$ undecyl α-methacrylate macromonomer ($C_1$-PEO-$C_1$-MA-40) was synthesized according to the protocol described by Liu et al. in *J. Macromol. Sci, Pure Appl. Chem.* (1996) A33, 3: 337.

For the synthesis of fluronic68-diacrylate, fluoric-68 is dissolved in dried $CH_2Cl_2$ with triethylamine. Under nitrogen environment, methacryloyl chloride was added drop-wise into the solution with stirring, then the solution was incubated in an ice bath for half an hour. The mixture was further stirred at room temperature overnight. The precipitated triethylammonium chloride was filtered, and the excess acryloyl chloride, $CH_2Cl_2$, and triethylamine were removed by rotary evaporation. The residue was dissolved in distilled chloroform and washed twice with saturated sodium bicarbonate solution. The chloroform solution was further washed twice with saturated brine. A solid product was recovered from the chloroform solution after evaporation. The pure product was obtained by re-precipitating the crude product three times from chloroform against ether.

2. Membrane Preparation

The porous membranes were prepared directly by microemulsion polymerization. Such microemulsions comprise variable amounts of HEMA, MMA, NIPAAm, ultra-pure water, and the surfactant $C_1$-PEO-$C_{11}$-MA-40 or fluronic68-diacrylate, the cross-linker EGDMA when $C_1$-PEO-$C_{11}$-MA-40 was used, as well as the photo-initiator DMPA.

Two 20 cm×20 cm glass plate were washed and dried at room temperature. The glass surfaces to be contacted with the microemulsions were polished using tissue with a small amount of silicon oil to enable removal of the polymer membrane after polymerization. About 1 g of each microemulsion was first poured onto a glass plate, and subsequently spread by slowly covering with another glass plate. This reduced the chances of air bubbles being trapped between the two glass plates. Small pieces of thin aluminum foil sheet were used as spacers between the glass plates to regulate the thickness of membranes.

The polymerization reaction was carried out in a UV reactor for 6 h. The membranes were immersed in de-ionized water, and the water was changed daily for one week before subjected to further characterization.

The compositions of formed membranes are set out in Table 1. The cross-linker EGDMA forms the remaining 2% of each composition.

TABLE 1

Composition of Selected Microemulsion Systems

| | Composition by Weight % | | | | |
|---|---|---|---|---|---|
| System | HEMA | MMA | NIPAA | Surfactant | Water |
| HMN 1 | 10 | 10 | 20 | 35 | 23 |
| HMN 2 | 20 | 10 | 10 | 35 | 23 |
| HMN 2a | 15 | 7.5 | 7.5 | 35 | 33 |
| HMN 3 | 10 | 20 | 10 | 35 | 23 |
| HMN 4 | 5 | 10 | 25 | 35 | 23 |
| HMN 5 | 10 | 0 | 30 | 35 | 23 |
| HMN 6 | 5 | 25 | 10 | 35 | 23 |

3. Topography Analysis

Investigation of the surface topographies of the membranes was conducted using a Thermo Microscope Autoprobe CP Research atomic force microscope (AFM system (Park Scientific Instrument, Sunnyvale, Calif.) in contact mode. Conical silicon nitride tips mounted on a silicon cantilever with a force constant of 0.40 N/m were employed. The $Si_8N_4$ cantilevers (with an integral tip) had a length of 180 μm, width of 38 μm, thickness of 1 μm and resonant frequency of 45 kHz. Each image contains 521×512 data points. The surface topographical images were processed using IP2.1 Image Software.

Cross-sectional topography of the membranes was investigated using a JEOL 6700 field emission gun scanning electronic microscope (FEG-SEM). The membranes were freeze-fractured in liquid nitrogen to expose the cross-sections. Prior to examination, the samples were vacuum dried at room temperature for 24 hrs before being coated with a thin layer of gold using a JEOL ion-sputter JFC-1100 gold-coating machine.

Figure 2:
FIG. 2 is a scanning electron microscopy image of a cross-section of a thermosensitive porous membrane.

As shown in FIG. 1, the surface topography analysis demonstrated that the membrane surface contained pores, typically less than 100 nm. A scanning electron micrograph of cross-section of the membrane, shown in FIG. 2, revealed the randomly distributed nanostructured channels created by the water content during the fabrication process, the channels being 50 to 100 nm in diameter.

4. Thermal Properties

The decomposition temperatures of polymeric membranes were analyzed by a Perkin Elmer thermogravimetric analyzer (TGA). The thermal behaviour of about 10 mg sample placed in a platinum cell, was evaluated from 30° C. to 800° C. A temperature gradient of 10° C./min was applied under dry nitrogen flow and the weight loss was continuously recorded. The temperature range where the sample weight decreased sharply was regarded as the decomposition temperature.

The thermal analysis showed that membranes having different monomer compositions had similar decomposition temperatures ($T_d$) ranging from 300° C. to 350° C. This result indicates that the membranes are thermally stable up to 300° C. and that alteration of the microemulsion composition does not affect the thermal stability of the resultant membranes. This thermal stability is a significant advantage as it would mean that the membranes can be sterilized by autoclaving or other means prior to clinical application.

5. Swelling Properties

The equilibrium swelling ratios ("ESR") of polymeric membranes were measured using pre-weighed dry samples, which were immersed in distilled water to equilibriun at various temperatures. After the excess surface water was removed with filter paper. The weight of fully swollen samples was recorded. ESR was determined according to the equation ESR (%)=(Ws−Wd)/Ws×100, where Wd refers to the dry sample weight and Ws is the wet sample weight after swelling equilibrium.

Figure 3:
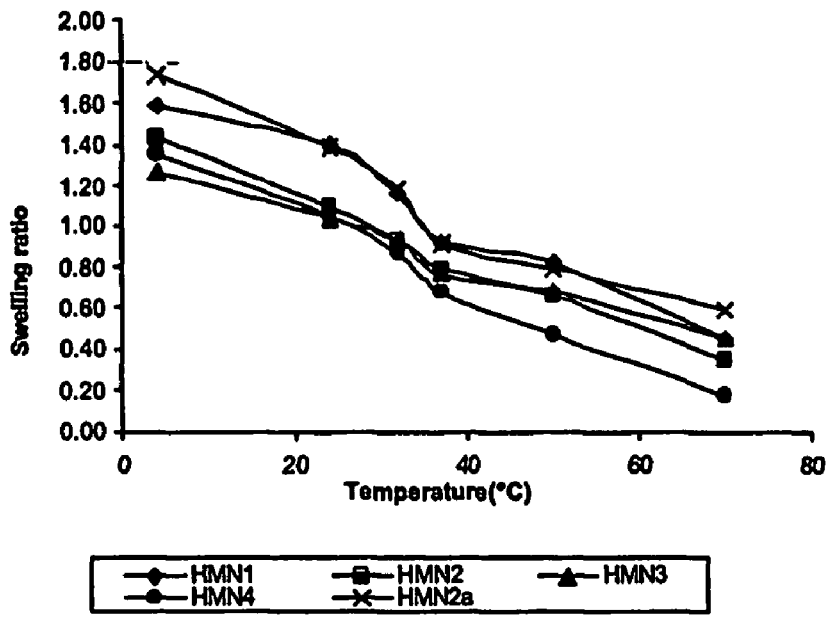
FIG. 3 is a graph of the swelling ratio of membranes with various monomer compositions versus temperature, to demonstrate the temperature-dependent swelling property of the membranes.

The membranes exhibited temperature-dependent swelling ratios (FIG. 3). They appeared to swell to a higher degree at low temperatures. A discontinuous decrease of swelling ratio took place in the range of 32 to 37° C., suggesting that the swelling behaviour is likely affected by the LCST of PNIPAAm. At ambient temperatures above this temperature range, the hydrophilicity of the membranes decreased, leading to lower swelling ratios. In general, an increased NIPAAm monomer content in the microemulsion improved the sensitivity of the membranes to temperature.

The water content as a percentage of the total membrane weight was measured at a range of temperatures for various membranes, as shown in Table 2.

TABLE 2

Water Content of Select Nanoporous Membranes

| | Water Content by Weight % | | | |
|---|---|---|---|---|
| System | 4° C. | 24° C. | 32° C. | 37° C. |
| HMN 1 | 61.4 | 58.3 | 53.8 | 48.0 |
| HMN 2 | 58.9 | 52.1 | 48.3 | 44.2 |
| HMN 3 | 55.9 | 51.0 | 48.8 | 43.3 |
| HMN 4 | 57.6 | 51.2 | 46.7 | 40.4 |
| HMN 5 | 70.8 | 63.9 | 59.1 | 56.0 |
| HMN 6 | 57.3 | 53.2 | 50.6 | 47.1 |

6. Water Vapour Transmission Rate

The water vapor transmission rate (WVTR) of the membranes was determined according to the ASTM E96 water method. Briefly, membrane discs in diameter of 16 mm were each mounted, with the aid of water impermeable sealant onto a plastic container containing 10 mL of distilled water, which was placed in an inverted position such that water could evaporate through the membrane into an environmental chamber. The container was weighed periodically to determine the rate of water movement across the membrane sample into the environmental chamber, which had a temperature of 32° C. and relative humidity of 50%. The WVTR was calculated from the equation WVTR=W/(t×A), where W is the weight of the water vapor transmitted through the membrane sample having area A at time t. The observed WVTR values for certain membranes is shown in Table 3.

TABLE 3

Water Vapour Transmission Rate of Select Nanoporous Membranes

| System | WVTR (g/m²/day) |
|---|---|
| HMN 1 | 509.3 |
| HMN 2 | 518.8 |
| HMN 2a | 862.6 |
| HMN 3 | 502.9 |
| HMN 4 | 531.6 |

7. Mechanical Properties

From an engineering perspective, good mechanical properties would allow materials used for wound dressings to maintain their shape during application. Here, three parameters, tensile strength, maximum percentage strain and Young's modulus, were measured to determine the mechanical properties of the nanostructured membranes.

The strain (%) at break, Young's Modulus and tensile strength of the membranes were measured by an Instron microforce tester. Samples with standard size stated in ASTM 638 were used. The tensile rate was 0.25 mm/min.

Membranes with different compositions were found to differ in mechanical behavior (Table 4). Their tensile strengths varied from 4.8 to 6.9 MPa, with the highest found in HMN 2. Membranes that only contained NIPAAm and HEMA demonstrated higher tensile strength and Young's modulus, although their percentage strain at the break point was compromised. This may be due to the strong hydrophilic interaction between the polymer chains. With the addition of MMA into the microemulsion, the membranes lost some of their tensile strength but their percentage of elongation increased to a range of 48 to 86%. In comparison, the tensile strength and Young's modulus of skin are normally 2.5 to 16 MPa and 6 to 40 MPa, respectively. Polymers with similar strengths and slightly higher Young's moduli are most frequently used to replace skin tissue (Silve, in *Biomaterials, Medical Devices and Tissue Engineering: An Integrated Approach*, Chapman & Hall, United Kingdom, 1994, 46.). The fact that the tensile strength of the nanostructured membranes ranges from 4.8 to 6.9 MPa and that the Young's modulus ranges from 140 to 380 Mpa suggests that these membranes have sufficient durability to be used as wound dressings.

TABLE 4

Mechanical Properties of Selected Membranes Dried

| System | Tensile Strength (MPa) | Young's Modulus (MPa) | % Strain at Break |
|---|---|---|---|
| HMN 1 | 5.7 ± 0.51 | 180 ± 30 | 74.4 ± 4.31 |
| HMN 2 | 6.9 ± 0.55 | 380 ± 40 | 78.0 ± 5.40 |
| HMN 3 | 5.9 ± 0.21 | 160 ± 10 | 86.9 ± 4.34 |
| HMN 4 | 4.8 ± 0.78 | 140 ± 20 | 48.6 ± 2.10 |
| HMN 5 | 10.9 ± 1.2 | 0.45 ± 0.05 | 40.2 ± 3.81 |
| HMN 6 | 6.2 ± 0.50 | 0.2 ± 0.03 | 58.8 ± 7.14 |

Mechanical properties of membranes in the swollen state were also investigated. HMN 1 and HMN 4 had reduced mechanical properties after wetting, while HMN 2 and HMN 3 retained their tensile strength and most of their flexibility (Table 5).

TABLE 5

Mechanical Properties of Selected Membranes After Wetting

| System | Tensile Strength (MPa) | Young's Modulus (MPa) | % Strain at Break |
|---|---|---|---|
| HMN 1 | 3.8 ± 0.43 | 110 ± 10 | 34.2 ± 5.99 |
| HMN 2 | 4.9 ± 0.55 | 280 ± 30 | 61.0 ± 3.10 |
| HMN 3 | 5.7 ± 0.21 | 100 ± 10 | 53.9 ± 3.04 |
| HMN 4 | 2.45 ± 0.25 | 120 ± 30 | 20.1 ± 1.57 |
| HMN 5 | 3.3 ± 0.36 | 190 ± 30 | 17.23 ± 1.87 |
| HMN 6 | 3.9 ± 0.23 | 100 ± 20 | 44.4 ± 3.64 |

8. Cell Viability Studies Upon Contact with Solid Membranes

To prepare the membranes for in vitro cytotoxicity studies, the membranes were cut into 2×2 mm pieces and soaked in PBS solution overnight. After being dried in 70° C. oven, they were autoclaved for use in the cytotoxicity study. Preliminary studies were done on membranes having various original monomer concentrations. EL4 cells (a C57BL/6J mouse lymphoma cell line) were incubated for 24 and 48 hours before viable cells were counted. There were 3 replicates for control (cells without specimens) and specimens. Results are expressed as percentage of viable relative to control.

After 24 and 48 hours incubation with the membranes, cells exhibited between 107.5 to 60.8 and 104.5 to 69.2% viability, respectively (Table 6). The increase of viablity of the cells in some of the trials may signal a period of acclimatization after which the cells adapt and resume normal growth.

TABLE 6

Viability of EL4 Cells After Exposure to Selected Membranes

| | Viability (% Control) | |
|---|---|---|
| System | 24 hrs | 48 hrs |
| HMN 1 | 105.4 | 98.4 |
| HMN 2 | 107.5 | 104.5 |
| HMN 3 | 96.1 | 84.1 |
| HMN 4 | 60.8 | 69.2 |

9. Drug Loading

To determine if the membranes could be used to deliver therapeutics such as drugs to a wound site, the membranes were tested using the model drug scopolamine. The membranes were immersed in scopolamine base at a concentration of 1 g/100 mL at 4° C. for 3 days. The drug-loaded membranes were then air-dried before in vitro testing. The in vitro tests were carried out at 37° C. in PBS (pH 7.4) on a Vankel VK 7000 dissolution test station. At predetermined intervals, 1 mL sample was drawn for HPLC analysis and replaced with fresh PBS buffer.

Figure 4:
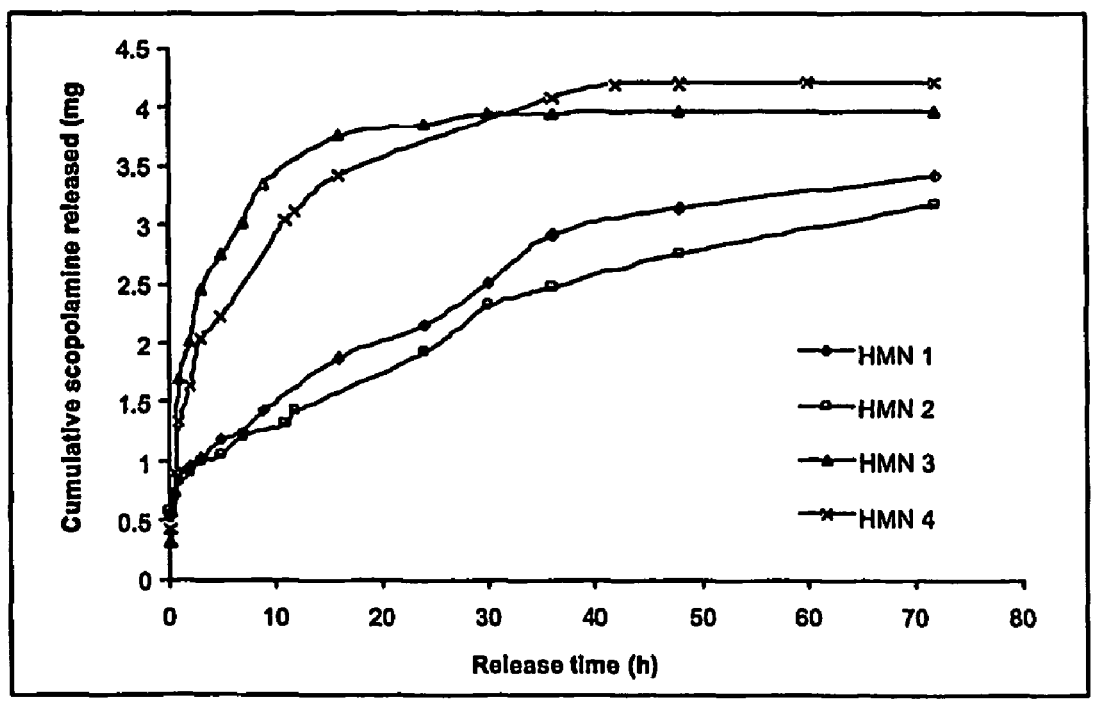
FIG. 4 is a plot of in vitro release profiles of a model drug, scopolamine, from scopolamine-loaded membranes.

A sustained release of scopolamine over 3 days was observed for HMN 1 and HMN 2 membranes (FIG. 4), indicating that the membranes are suitable for sustained delivery of drugs, such as antibacterial agents or wound healing accelerators, potentially resulting in greater efficiency of wound healing.

10. Cell Delivery from Membranes

The effect of temperature on cell detachment from the membranes was studied using mouse neoplastic fibroblast cells (L929, ATCC, USA). The membranes were autoclaved prior to use with cell cultures. In this experiment, each membrane was cut into the exact diameter of a well in a 24-well plate and then placed into test wells. The surface of the control wells was left unmodified. The L929 mouse fibroblast cells were then seeded onto the membranes, or well surface, at a density of $5 \times 10^5$ cells/mL and cultured at 37° C. under a humidified atmosphere of 5% $CO_2$. After about 48 hrs, the cultures were incubated at 4, 10, 15, 20 and 27° C. for half an hour as cold treatment Subsequently, the contents of each well were aspirated and transferred to a fresh 24-well plate. These flesh plates were then returned to the incubator to allow any detached cells to reattach and resume cell growth. Each well of the original plate was then washed gently with phosphate-buffered saline (PBS) at 25° C. and the viability of any remnant cells in each well was assessed using the MTT assay.

Figure 5:
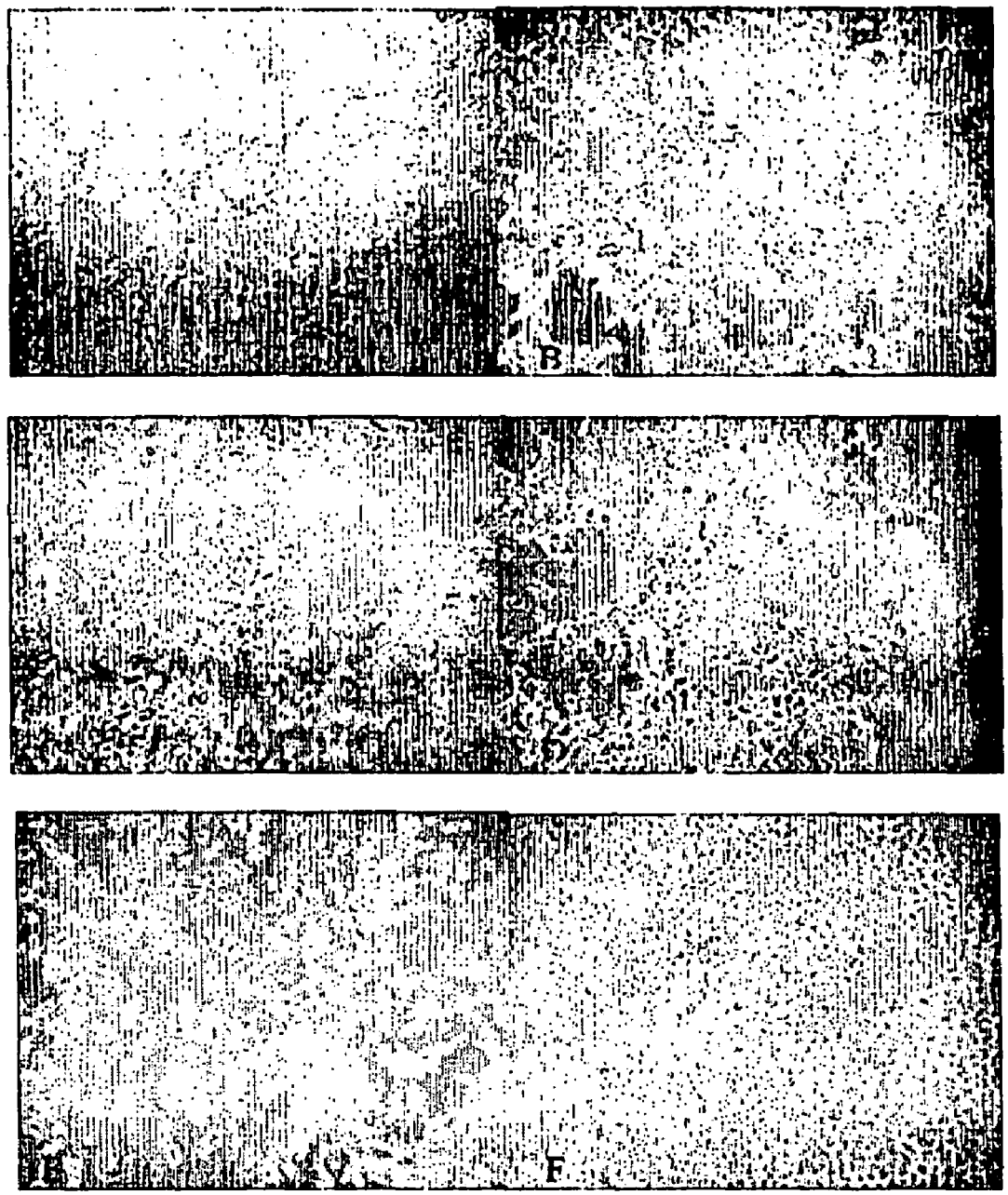
FIG. 5 is a photographic image of cells grown on membranes having different monomer compositions: (A) HMN 1; (B) HMN 2; (C) HMN 2a; (D) HMN 3; (E) HMN 4; and (F) cell culture plate.
Figure 6:
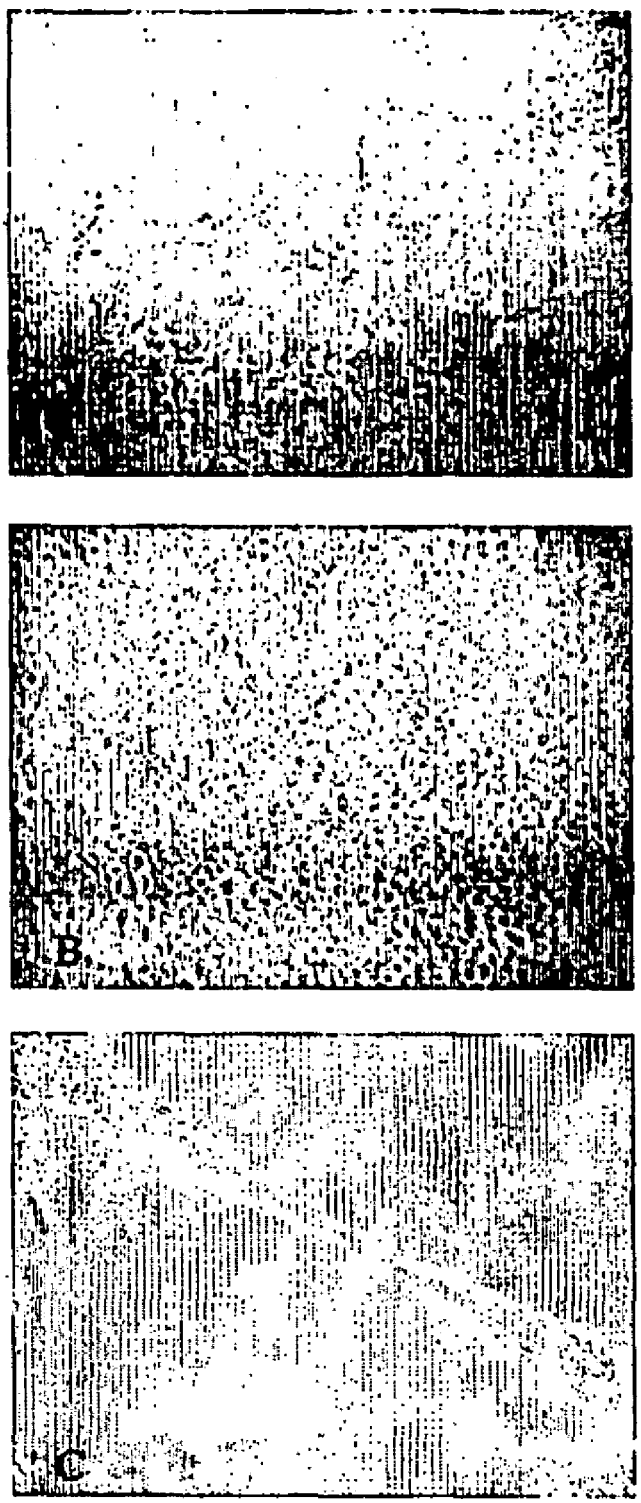
FIG. 6 is photographic images of cells grown on various surfaces: (A) thermosensitive porous membrane (HMN 1); (B) cell culture plate; and (C) a close up of cells connecting between clumps of growth on the membrane.

The cells were well attached onto the surface of all the membranes as shown in FIG. 5. The cells consistently organized themselves into aggregates connected by cytoplasmic projections (compare FIGS. 6B and 6C), a phenomenon not observed in the control samples.

Figure 7:
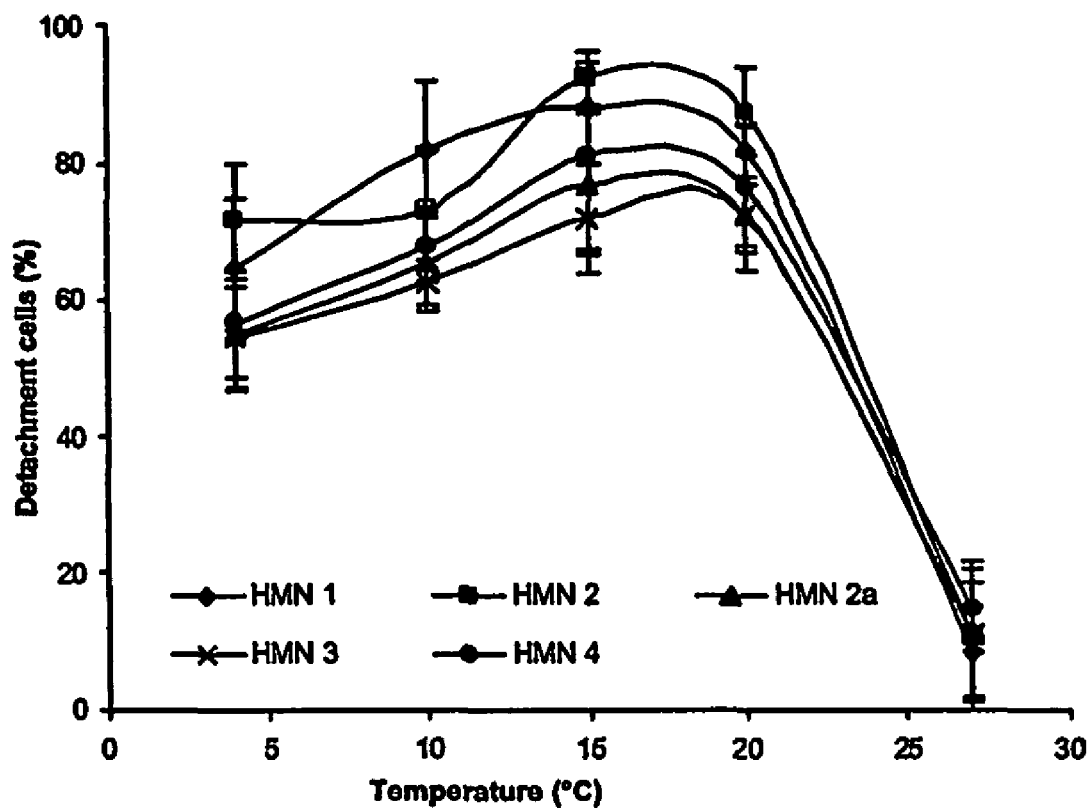
FIG. 7 is a plot of percentage of cells detached from various membranes as a function of temperature.
Figure 8:
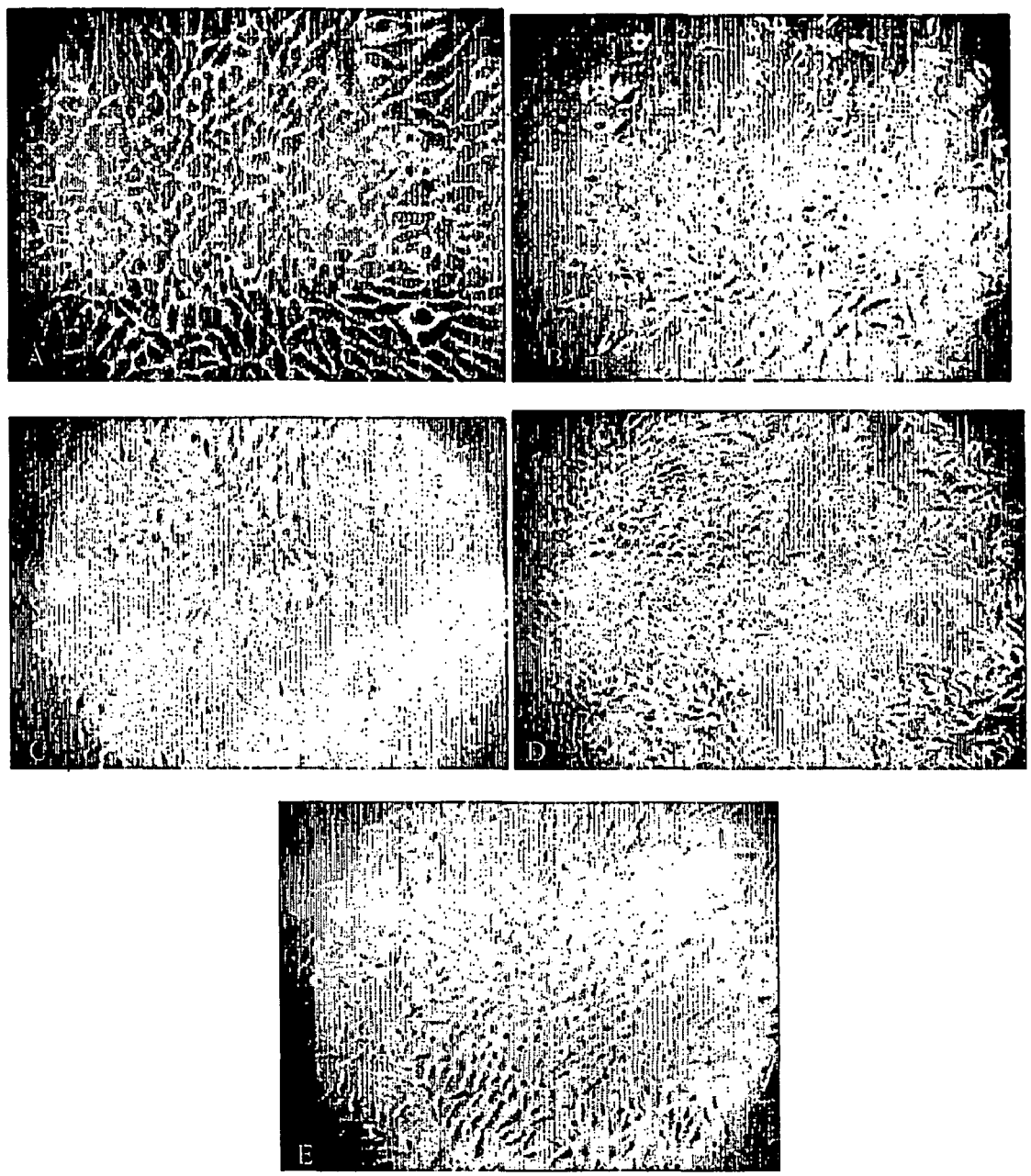
FIG. 8 is a photographic image of cells detached from the various membranes, reattached and grown on a culture plate: (A) HMN 1; (B) HMN 2; (C) HMN 2a; (1) HMN 3; and (E) HMN 4.

After incubation at 4° C. for about 30 minutes, 50 to 70% of the cells attached to the membranes were found to have detached. No apparent cell detachment was observed in the control plate. The effect of cooling temperature on the detachment was also investigated, as shown in FIG. 7. The maximum number of cells detached from the membranes at 15° C. However, it is noted that the effect of cooling temperature on the membrane may be vary for different types of cells, and with varying membrane composition. The cells that had detached from the thermosensitive membranes and that were transplanted attached to the new surface and resumed nominal growth (FIG. 8). This result demonstrates the viability of the detached cells and constitutes evidence against incipient cell death being the cause of the observed detachment. This property of the membranes indicates that the membranes are suitable for use as a vehicle for cell grafting.

Figure 9:
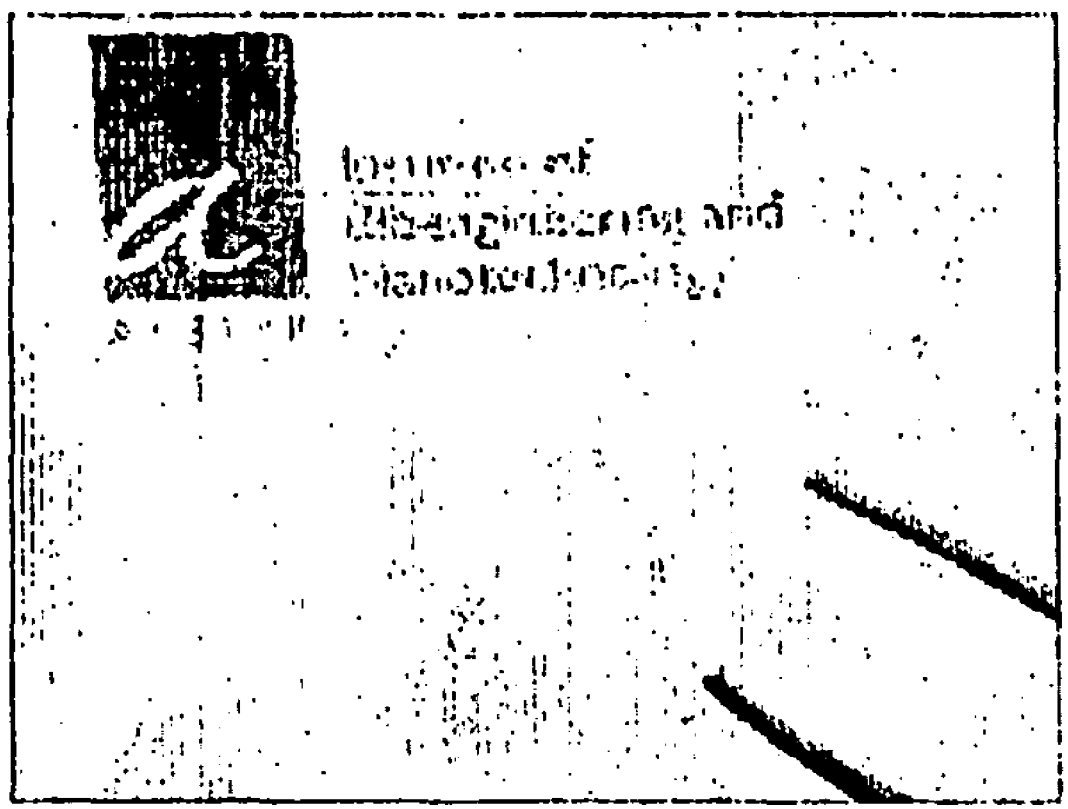
FIG. 9 is a photograph of a representative membrane, demonstrating the transparency of the membrane.

A representative membrane is shown in FIG. 9, demonstrating the transparency of the membrane, which would allow for visualization of the underlying wound.

As can be understood by one skilled in the art, many modifications to the exemplary embodiments described herein are possible. The invention, rather, is intended to encompass all such modification within its scope, as defined by the claims.

All documents referred to herein are fully incorporated by reference.

What is claimed is:

1. A process for preparing a thermosensitive nanoporous random polymer, the process comprising preparing a layer of a microemulsion of a desired thickness for a wound dressing, the microemulsion comprising a first monomer that is capable of forming a thermosensitive polymer and a polymerizable surfactant, and polymerizing the microemulsion, wherein the resulting polymer exhibits a temperature-dependent swelling ratio, the temperature-dependency being discontinuous around a lower critical solution temperature of the polymer.

2. The process of claim 1 wherein the first monomer is an alkylated acrylamide.

3. The process of claim 2 wherein the first monomer is N-isopropylacrylamide.

4. The process of claim 3 wherein the polymerizable surfactant is ω-methoxy poly(ethylene oxide)$_{40}$ undecyl α-methacrylate or poly(ethylene oxide)$_{78}$-poly(propylene oxide)$_{30}$-poly(ethylene oxide)$_{78}$-diacrylate.

5. The process of claim 4 wherein the microemulsion comprises a comonomer.

6. The process of claim 5 wherein the microemulsion comprises methyl methacrylate or 2-hydroxyethyl methacrylate.

7. The process of claim 6, wherein the polymerizable surfactant is ω-methoxy poly(ethylene oxide)$_{40}$ undecyl α-methacrylate and the microemulsion further comprises a chemical cross-linker.

8. The process of claim 7, wherein the cross-linker is ethylene glycol dimethacrylate.

9. The process of claim 8, wherein the microemulsion further comprises a photo-initiator.

10. The process of claim 9, wherein the photo-initiator is 2,2-dimethoxy-2-phenylacetophenone.

11. The process of claim 10, wherein the polymerizing comprises subjecting the microemulsion to ultraviolet radiation.

12. The process of claim 11, wherein the microemulsion comprises about 20% (w/w) N-isopropylacrylamide, about 10% (w/w) methyl methacrylate, about 10% (w/w) 2-hydroxyethyl methacrylate, about 35% (w/w) ω-methoxy poly (ethylene oxide)$_{40}$ undecyl α-methacrylate, about 23% (w/w) water and about 2% ethylene glycol dimethacrylate.

13. The process of claim 11, wherein the microemulsion comprises about 10% (w/w) N-isopropylacrylamide, about 10% (w/w) methyl methacrylate, about 20% (w/w) 2-hydroxyethyl methacrylate, about 35% (w/w) ω-methoxy poly (ethylene oxide)$_{40}$ undecyl α-methacrylate, about 23% (w/w) water and about 2% ethylene glycol dimethacrylate.

14. The process of claim 11, wherein the microemulsion comprises about 7.5 (w/w) N-isopropylacrylamide, about 7.5% (w/w) methyl methacrylate, about 15% (w/w) 2-hydroxyethyl methacrylate, about 35% (w/w) ω-methoxy poly (ethylene oxide)$_{40}$ undecyl α-methacrylate, about 33% (w/w) water and about 2% ethylene glycol dimethacrylate.

15. The process of claim 11, wherein the microemulsion comprises about 10% (w/w) N-isopropylacrylamide, about 20% (w/w) methyl methacrylate, about 10% (w/w) 2-hydroxyethyl methacrylate, about 35% (w/w) ω-methoxy poly (ethylene oxide)$_{40}$ undecyl α-methacrylate, about 23% (w/w) water and about 2% ethylene glycol dimethacrylate.

16. The process of claim 11, wherein the microemulsion comprises about 25% (w/w) N-isopropylacrylamide, about 10% (w/w) methyl methacrylate, about 5% (w/w) 2-hydroxyethyl methacrylate, about 35% (w/w) co-methoxy poly(ethylene oxide)$_{40}$ undecyl α-methacrylate, about 23% (w/w) water and about 2% ethylene glycol dimethacrylate.

17. The process of claim 11, wherein the microemulsion comprises about 30% (w/w) N-isopropylacrylamide, about 10% (w/w) 2-hydroxyethyl methacrylate, about 35% (w/w) ω-methoxy poly(ethylene oxide)$_{40}$ undecyl α-methacrylate, about 23% (w/w) water and about 2% ethylene glycol dimethacrylate.

18. The process of claim 11, wherein the microemulsion comprises about 10% (w/w) N-isopropylacrylamide, about 25% (w/w) methyl methacrylate, about 5% (w/w) 2-hydroxyethyl methacrylate, about 35% (w/w) ω-methoxy poly(ethylene oxide)$_{40}$ undecyl α-methacrylate, about 23% (w/w) water and about 2% ethylene glycol dimethacrylate.

* * * * *

UNITED STATES PATENT AND TRADEMARK OFFICE
CERTIFICATE OF CORRECTION

PATENT NO. : 8,394,366 B2
APPLICATION NO. : 10/564401
DATED : March 12, 2013
INVENTOR(S) : Yi Yan Yang and Li Shan Wang Page 1 of 1

It is certified that error appears in the above-identified patent and that said Letters Patent is hereby corrected as shown below:

In the Claims:

Column 16, Line 14: "N-isopropylacrylamide" should read -- $N$-isopropylacrylamide --

Column 16, Line 37: "N-isopropylacrylamide" should read -- $N$-isopropylacrylamide --

Column 16, Line 43: "N-isopropylacrylamide" should read -- $N$-isopropylacrylamide --

Column 16, Line 49: "N-isopropylacrylamide" should read -- $N$-isopropylacrylamide --

Column 16, Line 55: "N-isopropylacrylamide" should read -- $N$-isopropylacrylamide --

Column 16, Line 61: "N-isopropylacrylamide" should read -- $N$-isopropylacrylamide --

Column 16, Line 63: "co-methoxy" should read -- $\omega$-methoxy --

Column 16, Line 67: "N-isopropylacrylamide" should read -- $N$-isopropylacrylamide --

Column 17, Line 6: "N-isopropylacrylamide" should read -- $N$-isopropylacrylamide --

Signed and Sealed this
Second Day of December, 2014

Michelle K. Lee
*Deputy Director of the United States Patent and Trademark Office*